(12) United States Patent
Horvath et al.

(10) Patent No.: US 8,657,874 B2
(45) Date of Patent: Feb. 25, 2014

(54) METHOD FOR PHYSIOLOGIC CONTROL OF A CONTINUOUS FLOW TOTAL ARTIFICIAL HEART

(75) Inventors: David Horvath, Euclid, OH (US); Alex Massiello, Chesterland, OH (US); Leonard A. R. Golding, Chagrin Falls, OH (US); Barry Kuban, Avon Lake, OH (US)

(73) Assignee: Cleveland Clinic Foundation, Cleveland, OH (US)

( * ) Notice: Subject to any disclaimer, the term of this patent is extended or adjusted under 35 U.S.C. 154(b) by 1245 days.

(21) Appl. No.: 12/349,658

(22) Filed: Jan. 7, 2009

(65) Prior Publication Data

US 2010/0174231 A1 Jul. 8, 2010

(51) Int. Cl.
*A61M 1/10* (2006.01)

(52) U.S. Cl.
USPC .......................................... 623/3.1; 417/353

(58) Field of Classification Search
USPC .......................................... 623/3.1; 417/353
See application file for complete search history.

(56) References Cited

U.S. PATENT DOCUMENTS

| | | |
|---|---|---|
| RE28,742 E | 3/1976 | Rafferty et al. |
| 4,355,954 A | 10/1982 | Wilson |
| 4,381,901 A | 5/1983 | Labudde |
| 4,867,633 A | 9/1989 | Gravelle |
| 4,888,011 A * | 12/1989 | Kung et al. ................. 623/3.24 |
| 5,102,295 A | 4/1992 | Pope |
| 5,320,482 A | 6/1994 | Palmer et al. |
| 5,695,471 A | 12/1997 | Wampler |
| 5,840,070 A | 11/1998 | Wampler |
| 5,928,131 A | 7/1999 | Prem |
| 6,074,180 A | 6/2000 | Khanwilkar et al. |
| 6,080,133 A | 6/2000 | Wampler |
| 6,179,773 B1 | 1/2001 | Prem et al. |
| 6,193,473 B1 | 2/2001 | Mruk et al. |
| 6,234,998 B1 | 5/2001 | Wampler |
| 6,244,835 B1 | 6/2001 | Antaki et al. |
| 6,293,901 B1 | 9/2001 | Prem |
| 6,363,276 B1 | 3/2002 | Prem et al. |
| 6,368,083 B1 | 4/2002 | Wampler |
| 6,375,607 B1 | 4/2002 | Prem |
| 6,394,769 B1 | 5/2002 | Bearnson et al. |

(Continued)

OTHER PUBLICATIONS

Qian, K.X. et al, "A Novel Permanent Maglev Impeller TAH: Most Reuirements on Blood Pumps Have Been Satisfied", Journal of Biomaterials Applications, vol. 18, Jul. 2003, pp. 53-61.

(Continued)

*Primary Examiner* — Thomas J Sweet
*Assistant Examiner* — Matthew Schall
(74) *Attorney, Agent, or Firm* — Trego, Hines & Ladenheim, PLLC (57) ABSTRACT

A method is provided of controlling a pump including a electrical motor coupled to a rotor which carries first and second impellers at opposite ends thereof. The method includes: (a) driving the rotor using the motor, so as to circulate fluid from the first impeller through a first fluid circuit, the second impeller, a second fluid circuit, and back to the first impeller; (b) determining a resistance of the first fluid circuit, based on a first motor parameter; (c) determining a flow rate through the first fluid circuit based on a second motor parameter; and (d) varying at least one operational parameter of the pump so as to maintain a predetermined relationship between the flow rate and the resistance of the first fluid circuit.

10 Claims, 11 Drawing Sheets

(56) References Cited

U.S. PATENT DOCUMENTS

| | | |
|---|---|---|
| 6,422,990 B1 | 7/2002 | Prem |
| 6,511,298 B2 | 1/2003 | Takura et al. |
| 6,595,762 B2 | 7/2003 | Khanwilkar et al. |
| 6,619,935 B1 | 9/2003 | Kluth et al. |
| 6,688,861 B2 | 2/2004 | Wampler |
| 7,189,260 B2 | 3/2007 | Horvath et al. |
| 7,502,648 B2 | 3/2009 | Okubo et al. |
| 7,575,423 B2 | 8/2009 | Wampler |
| 2002/0102169 A1 | 8/2002 | Wampler |
| 2004/0234397 A1 | 11/2004 | Wampler |
| 2006/0183962 A1 | 8/2006 | Okubo et al. |
| 2007/0253842 A1 | 11/2007 | Horvath et al. |

OTHER PUBLICATIONS

Frazier et al., "Total Heart Replacement With Dual Centrifugal Ventricular Assist Devices", Asaio Journal 2005; 51:224-229.

* cited by examiner

METHOD FOR PHYSIOLOGIC CONTROL OF A CONTINUOUS FLOW TOTAL ARTIFICIAL HEART

BACKGROUND OF THE INVENTION

This invention relates generally to artificial hearts, and more particularly to methods of control therefor.

Heart transplant is a course of action for patients with end stage heart failure, a leading cause of premature death. Because of the unavailability of donor hearts, electromechanical blood pumping systems are being developed and are increasingly coming into use. These devices can provide a bridge to transplant, bridge to recovery, or as a permanent treatment for patients who may not receive a donor heart. Most such patients will be treated with a ventricular assist device ("VAD"), which draws blood from the left or right ventricle, and discharges to the aorta or pulmonary artery, respectively. Some patents require a total artificial heart (TAH) as either a bridge to transplant, or as a permanent therapy.

One known type of TAH is a continuous flow total artificial heart (CFTAH) which includes two centrifugal pumps on one rotor supported on a hydrodynamic bearing and driven by a single motor. The CFTAH replaces the ventricles of the heart, and delivers blood flow to both the systemic (left) and pulmonary (right) circulation of the patient. An example of such a CFTAH is described in U.S. Patent Application Publication 2007/0253842.

While this type of CFTAH can be operated under external control, there is a need for physiologic control therefor, preferably using the least number of sensors.

BRIEF SUMMARY OF THE INVENTION

This need is addressed by the present invention, which provides a system and method for physiologic control of an artificial heart.

According to one aspect of the invention, a method is provided of controlling a pump including a electrical motor coupled to a rotor which carries first and second impellers at opposite ends thereof The method includes: (a) driving the rotor using the motor, so as to circulate fluid from the first impeller through a first fluid circuit, the second impeller, a second fluid circuit, and back to the first impeller; (b) determining a resistance of the first fluid circuit, based on a first motor parameter; (c) determining a flow rate through the first fluid circuit based on a second motor parameter; and (d) varying at least one operational parameter of the pump so as to maintain a predetermined relationship between the flow rate and the resistance of the first fluid circuit.

According to another aspect of the invention, and artificial heart system includes: (a) an artificial heart including a electrical motor coupled to a rotor which carries first and second impellers at opposite ends thereof, where: (i) the first impeller communicates with a patient's systemic vasculature; and (ii) the second impeller communicates with the patient's pulmonary vasculature; (b) a power source; and (c) a controller coupled to the power source and the pump, the controller programmed to: (i) drive the rotor using the motor, so as to pump blood in a circuit from the first impeller through the pulmonary vasculature, the second impeller, the systemic vasculature, and back to the first impeller; (ii) determine a resistance of the systemic vasculature, based on a first motor parameter; (iii) determine a flow rate through the systemic vasculature based on a second motor parameter; and (iii) vary at least one operational parameter of the artificial heart so as to maintain a predetermined relationship between the systemic flow and the resistance of the systemic vasculature.

According to another aspect of the invention, a method is provided for controlling a pump including a electrical motor coupled to a rotor which carries first and second impellers at opposite ends thereof. The method includes: (a) driving the rotor using the motor, so as to circulate fluid from the first impeller through a first fluid circuit, the second impeller, a second fluid circuit, and back to the first impeller; (b) modulating the speed of the rotor to generate a pulsatile flow; (c) monitoring a motor parameter indicative of suction or rubbing; and (d) in response to an indication of suction or rubbing, reducing the peak motor speed.

BRIEF DESCRIPTION OF THE DRAWINGS

The invention may be best understood by reference to the following description taken in conjunction with the accompanying drawing figures in which.

DETAILED DESCRIPTION OF THE INVENTION

Figure 1:
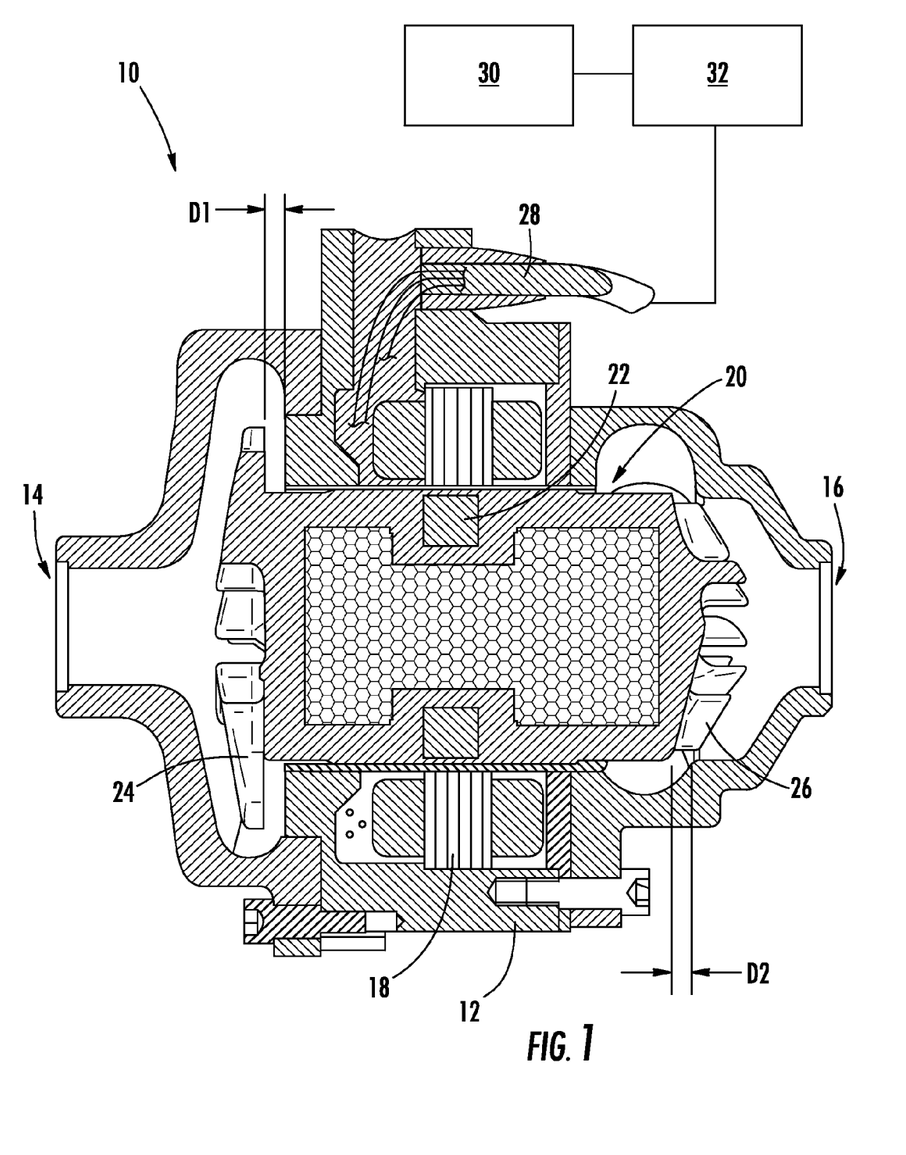
FIG. 1 is a cross-sectional view of an artificial heart and control system constructed according to an aspect of the present invention.

Referring to the drawings wherein identical reference numerals denote the same elements throughout the various views, FIG. 1 depicts a continuous flow total artificial heart 10 used to temporarily or permanently support an human patient. The artificial heart 10 includes a hollow housing 12 with opposed left and right inlets 14 and 16. An electrical stator 18 comprising a plurality of coil windings is disposed in the housing 12. While a total artificial heart 10 is used as an illustrative example, the principles of the present invention are equally applicable to other kinds of mechanical configurations and pumps, for example ventricular assist devices.

A rotor 20 is disposed inside the stator 18. The rotor 20 includes a magnet assembly 22 comprising one or more permanent magnets arranged in an annular configuration. A left impeller 24 comprising an annular array of vanes is carried at the left end of the rotor 20 adjacent the left inlet 14. A right impeller 26 comprising an annular array of vanes is carried at the right end of the rotor 20 adjacent the right inlet 16. The left and right impellers 24 and 26 discharge into separate right and left peripheral outlets, which are not shown in FIG. 1. The left impeller 24 along with the portion of the housing 12 surrounding it may be referred to as a "left pump" while the right impeller 26 along with the portion of the housing 12 surrounding it may be referred to as a "right pump".

All of the portions of the artificial heart 10 which will come into contact with blood or tissue are constructed from known biologically compatible materials such as titanium, medical grade polymers, and the like.

The rotor 20 and the stator 18 operate as a brushless DC motor through the application of varying electrical currents to the stator 18. The artificial heart 10 is coupled by a cable 28 to a controller 32, which is in turn powered by a power source 30, for example a battery, both of which are shown schematically in FIG. 1. The controller 32 is effective to provide pulsed DC current to the stator 18 in a known manner, and includes a microprocessor or other hardware suited to carry out a preprogrammed control method, as described in more detail below. The controller 32 may include subcomponents such as a CPU or main processor coupled to a known type of motor driver circuit. The degrees of freedom for the controller 32 are mean pump speed (RPM), DC pulse rate, speed pulsatility (i.e. RPM modulation about the mean), and/or duty cycle. The controller 32 is further configured to measure one or more control parameters, in particular electrical power (wattage) delivered to the artificial heart 10, and to receive a feedback signal from the artificial heart 10 indicative of the pump speed. Speed pulsatility (i.e. RPM modulation) may be used to create a pulse in a patient, and also provide an additional parameter for physiologic control.

Figure 2:
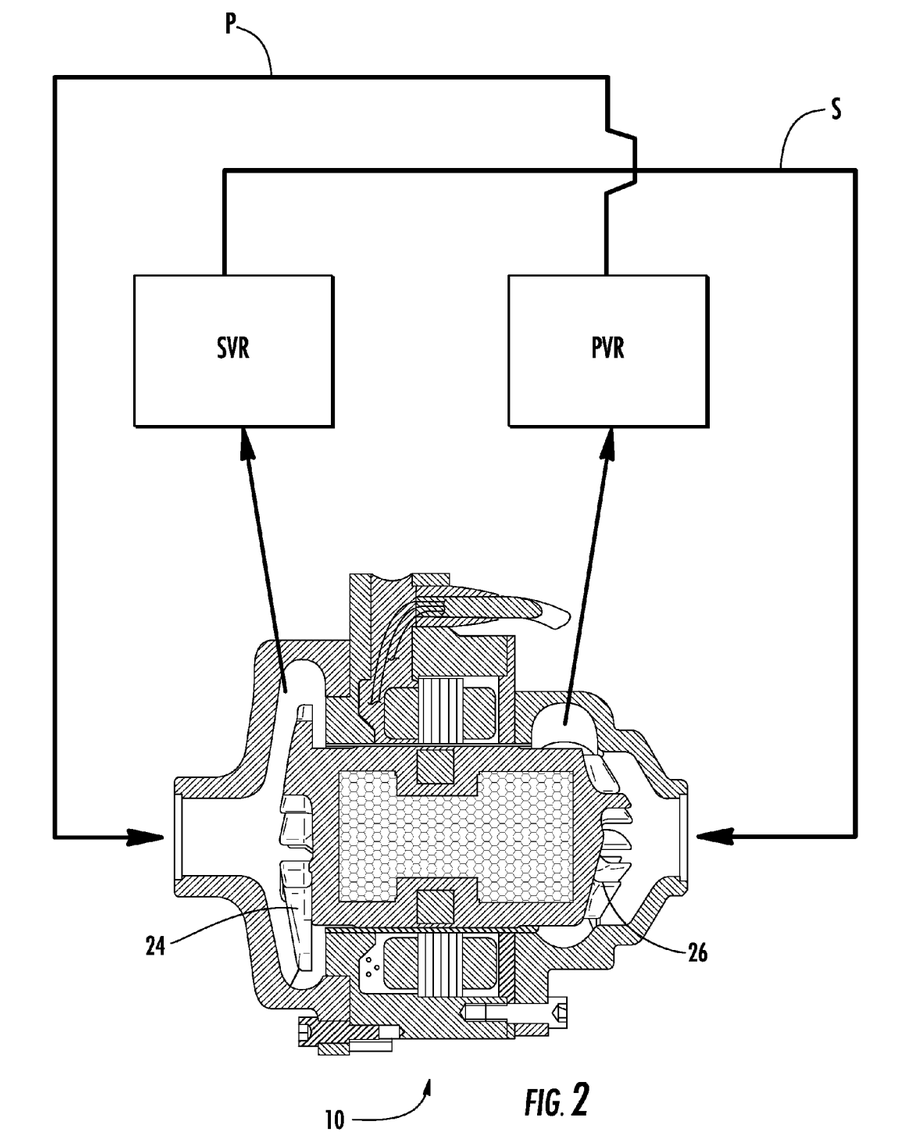
FIG. 2 is schematic block diagram of the pump of FIG. 1 coupled to a circulatory system.

FIG. 2 shows a simplified schematic of the artificial heart 10 coupled to a patient's circulatory system. In operation, the left impeller 24 pushes blood through the body's systemic vasculature, which defines a fluid circuit "S" and is represented from a hydraulic standpoint by a systemic vascular resistance labeled "SVR". Blood then flows back to the right atrium (right impeller inlet). The right impeller 26 pushes the blood through the body's pulmonary vasculature, which defines another fluid circuit "P" and is represented from a hydraulic standpoint by a pulmonary vascular resistance labeled "PVR". Blood flows from the PVR back to the left atrium (left impeller inlet).

If the systemic (i.e. left) flow is lower than the pulmonary (i.e. right) flow, then the left atrial pressure increases, and the right atrial pressure decreases. If the left output is greater than the right, then the atrial pressures reverse. Thus, an unbalance in flows is automatically accompanied by an unbalance in atrial (pump inlet) pressures.

The magnet assembly 22 in the rotor 20 is axially shorter than the stator 18, allowing a degree of free axial movement of the rotor 20, in response to any unbalance of pump inlet (i.e. atrial) pressures. This axial movement changes the distances "D1" and "D2" (see FIG. 1) which represent axial operating clearances of the left impeller 24 and right impeller 26, respectively. This change in pump geometry affects the relative left/right performance in a direction to correct the atrial pressure imbalance. Thus, the artificial heart 10 is self-balancing, acting as an inlet pressure balancing regulator while at the same time pumping both systemic and pulmonary circulation.

The artificial heart 10 is controlled as follows. First, a desired or targeted characteristic is determined by a physician. The characteristic describes the relationship between the volumetric flow rate in the systemic vasculature S and the SVR. In the example shown in FIG. 3, the characteristic is a linear plot between endpoints selected by the physician.

Figure 4:
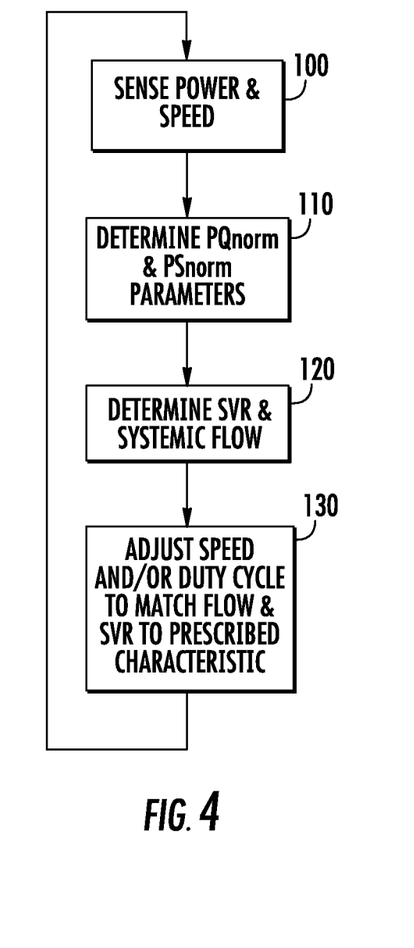
FIG. 4 is a block diagram showing a method of controlling a pump in accordance with an aspect of the present invention.

Referring to FIG. 4, the controller 32 delivers power to the artificial heart 10 to spin the left and right impellers 24 and 26. The speed of the rotor pulse may be modulated in order to create a pulse in the patient. As used herein, "modulation" refers generally to any change in a cyclic property of the rotor speed, whether this change is made directly or indirectly, and may be accomplished by various means. For example, direct closed loop control of the rotor speed may be implemented. Alternatively, the electrical current supplied to the motor from the controller 32 may be modulated, and the resulting changes in rotor speed accepted. The rotor modulation signal (i.e. the speed or current wave form) may be sinusoidal, or a sine wave with a duty cycle transformation, or other wave forms such as ramp, triangular, or square. At block 100, the controller 32 senses the average power (wattage) delivered to the motor, which can be measured by the controller 32 in a known manner, and the rotor speed, based on a feedback signal from the motor.

Next, at block 110, the controller 32 computes two parameters: PSnorm, which is defined as average Watts divided by kRPM$^3$, and PQnorm, defined as average Watts divided by kRPM$^2$.

Figure 5:
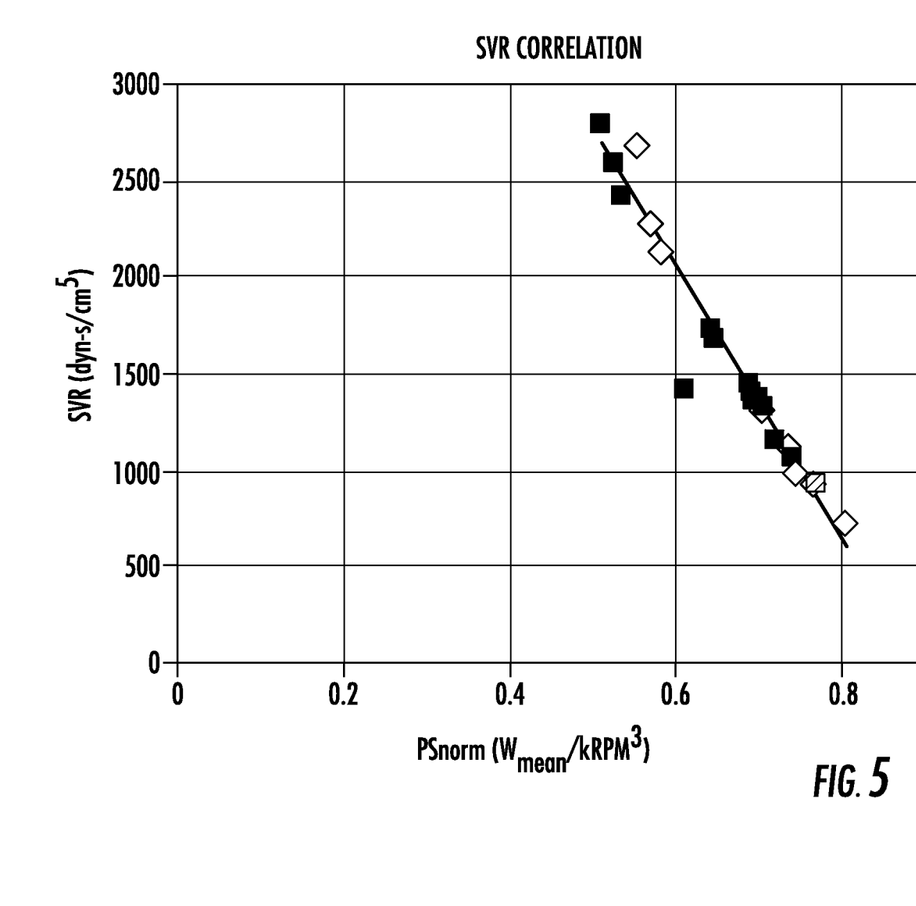
FIG. 5 is a graph showing observed systemic vascular resistance values plotted against a first measured motor power characteristic.

Next, at block 120, the SVR and the systemic flow rate are determined based on the computed parameters. FIG. 5 shows a sample of a suitable correlation for SVR (in dyn·s/cm$^5$) vs. PSnorm. The correlation is derived from empirical test data. It is depicted as a graph in FIG. 5, but it may be implemented or stored by the controller 32 in any equivalent fashion, for example as a graph, as a lookup table or matrix, or as a mathematical expression (e.g. a linear or polynomial curve fit).

Figure 6:
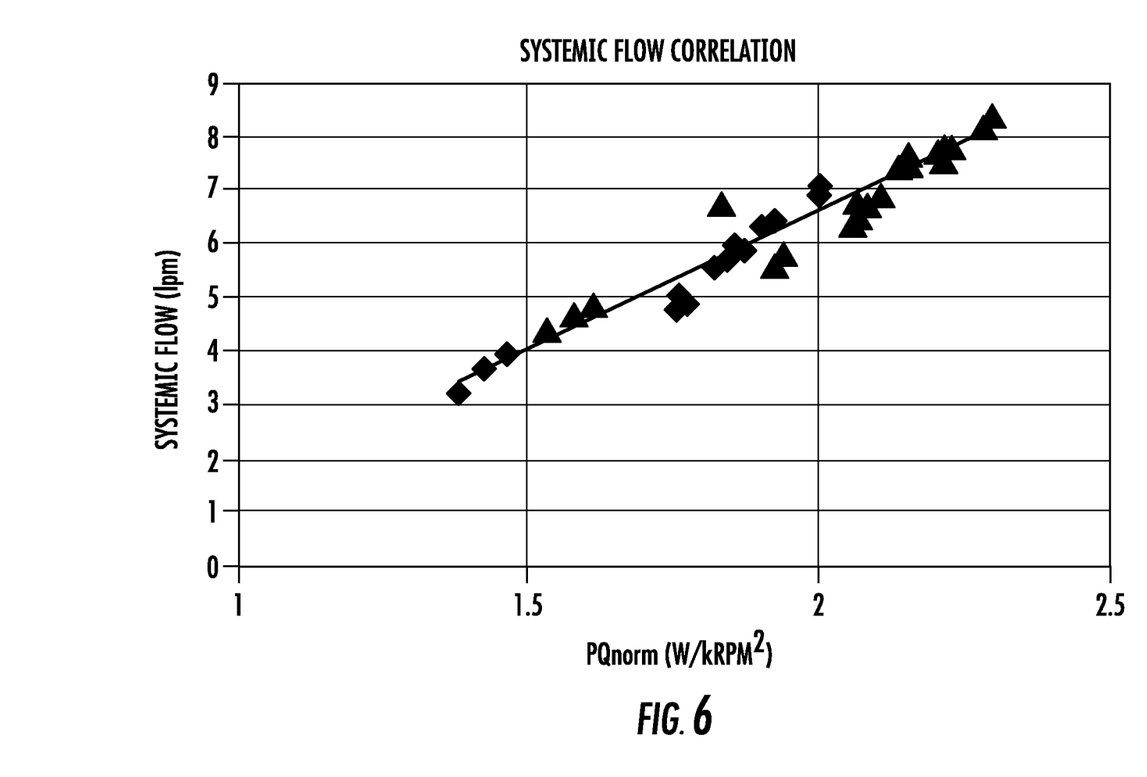
FIG. 6 is a graph showing observed systemic flow values plotted against a second measured motor power characteristic.

FIG. 6 shows a sample of a suitable correlation for systemic flow rate (in lpm) vs. PQnorm. The correlation is derived from empirical test data. It is depicted as a graph in FIG. 6, but it may be implemented or stored by the controller 32 in any equivalent fashion, for example as a graph, as a lookup chart or matrix, or as a mathematical expression (e.g. a linear or polynomial curve fit).

Figure 3:
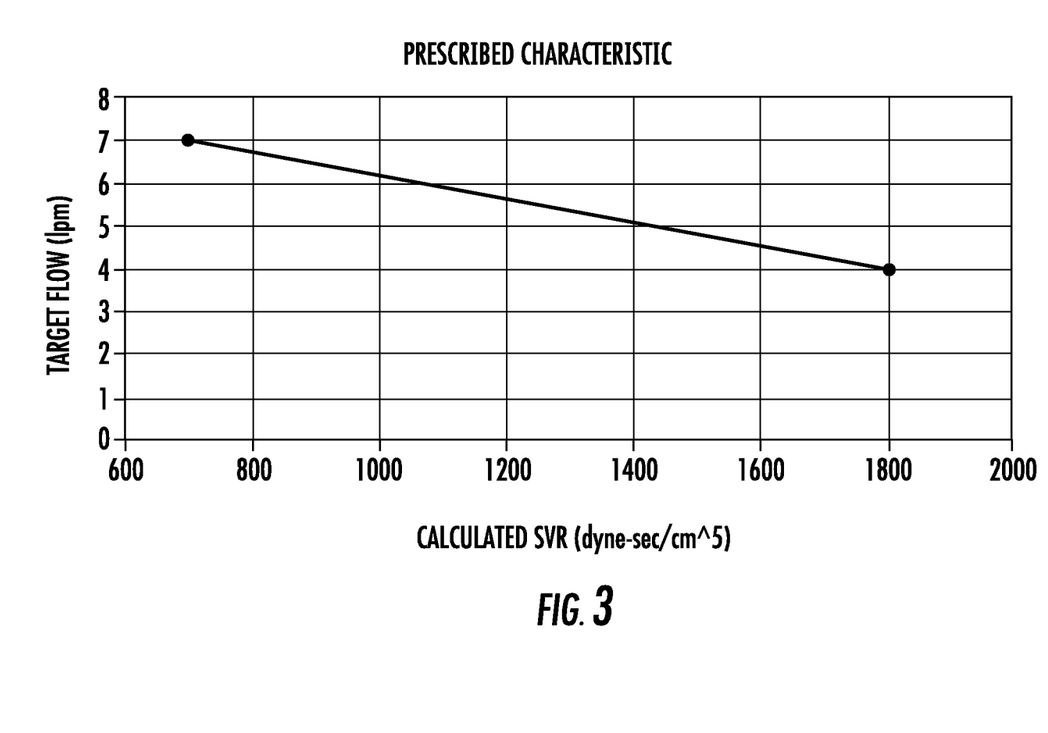
FIG. 3 is a graph showing a target operating characteristic.

Once the systemic flow rate and SVR have been determined, their relationship can be computed to determine if the current operating point lies on the prescribed characteristic shown in FIG. 3. If it does not, then one or more operational variables are increased or decreased until it does, at block 130. Examples of such operation variables include mean pump speed, pulse rate, speed pulsatility, and/or duty cycle. The process repeats at block 100 so long as pump operation continues.

Figure 7:
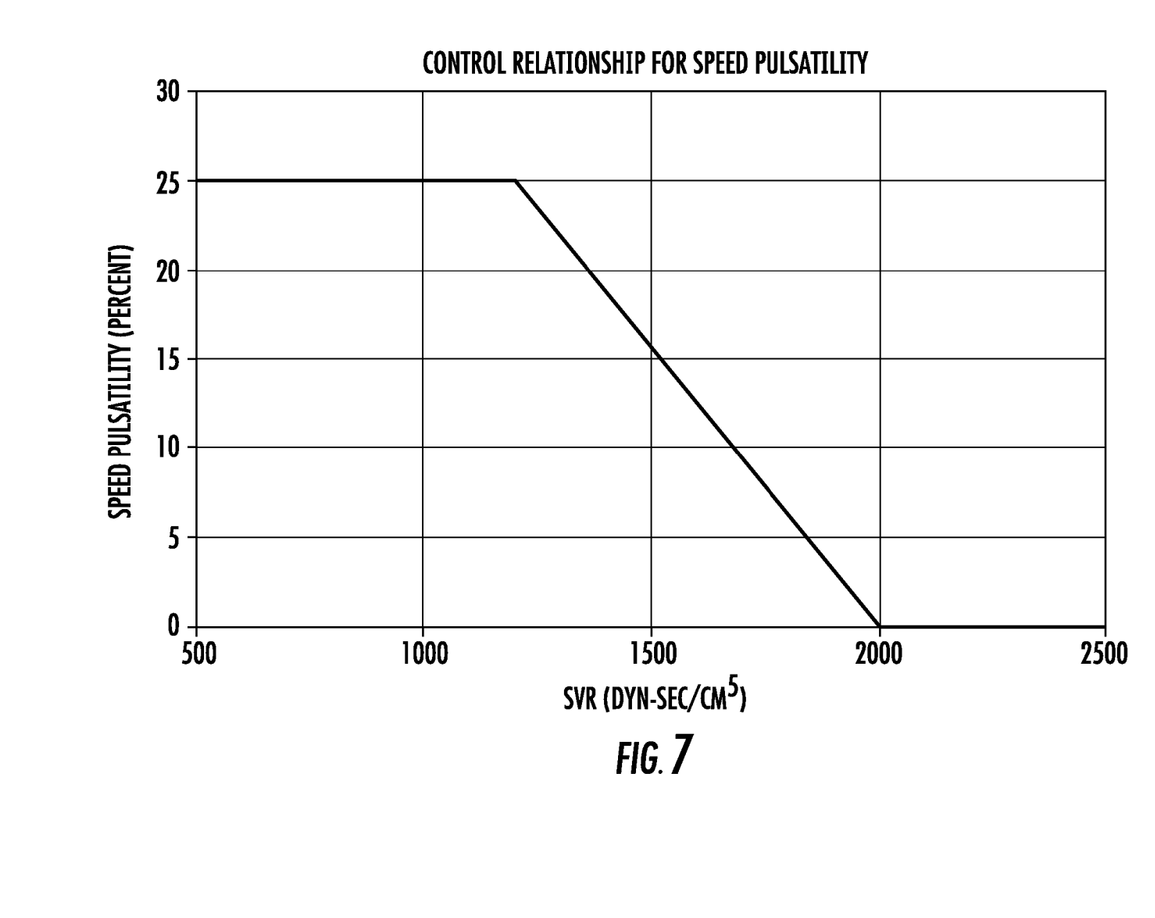
FIG. 7 is a graph showing a control relationship for speed pulsatility.

Independent of the control process, the self-balancing process described above is also taking place during operation of the artificial heart 10. The relative left/right performance of the two pumps can be further affected by the relative impedance seen by the pump outputs. In this pump configuration, speed modulation at high SVR can decrease the left pump output while increase the right pump output. This effect can be moderated by using the controller 32 to reduce or eliminate any speed pulsatility at high SVR values. For example, the controller 32 may be programmed to follow a characteristic of enforced speed pulsatility vs. SVR similar to the example shown in FIG. 7. This allows the artificial heart 10 to self-balance over a wider range of physiologic conditions, allowing an additional degree of freedom in balancing left/right performance.

Operating the artificial heart 10 in a modulated mode can cause an intermittent suction of tissue around one of the left or right inlets 14 or 16 at the cyclic peak speed with physiologic decreases in blood volume returning to the artificial heart 10. This intermittent occlusion can cause erratic and amplified oscillation in axial movement of the rotor 20, and touching of the left or right impellers 24 or 26 against the pump housing 12, which is reflected in the speed and current signals processed in the controller 32. Intermittent suction and the associated effects are undesirable and can cause excessive wear or damage to the artificial heart 10. In addition to control of the artificial heart 10, the present invention provides a method for detecting this intermittent suction and responding to it through peak speed reduction.

Figure 8:
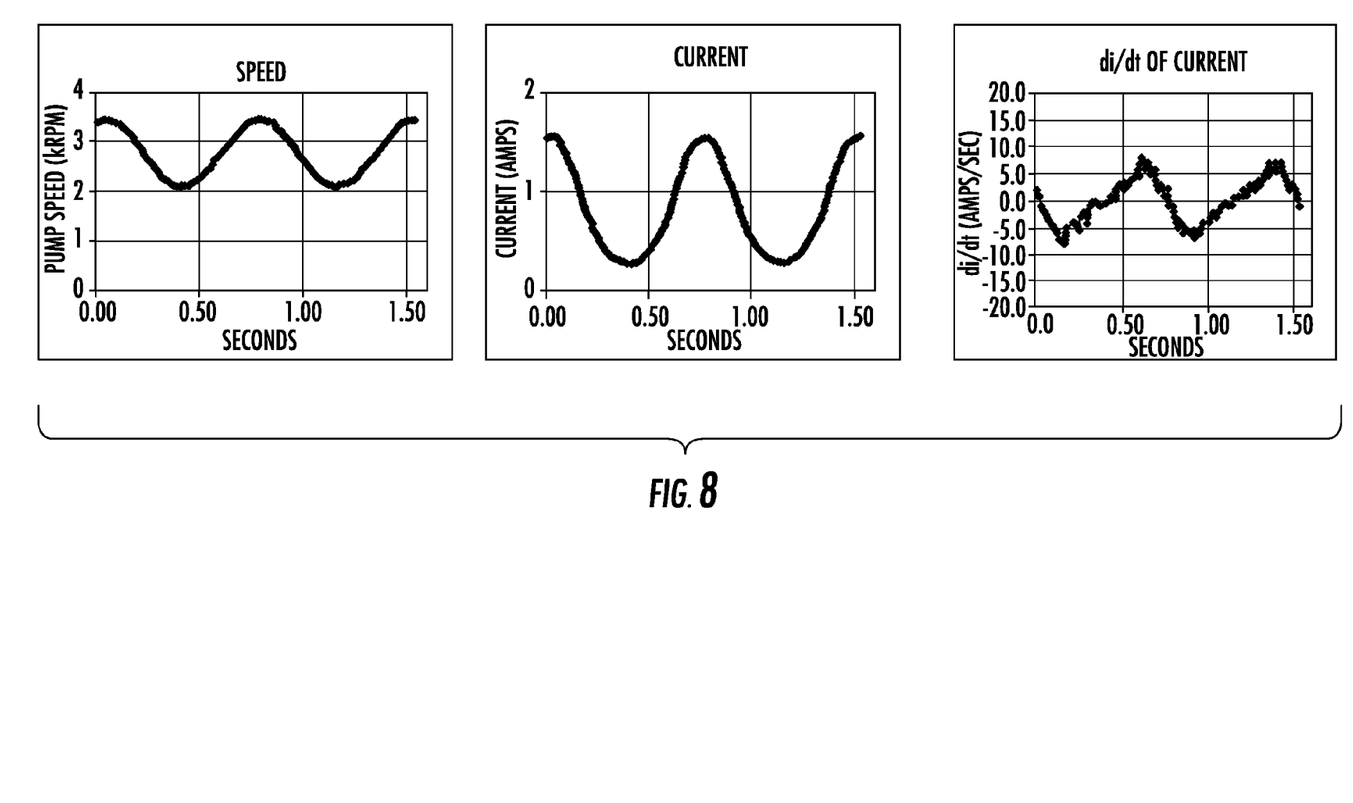
FIG. 8 is a set of graphs showing operation of an artificial heart with modulated speed under normal conditions.
Figure 9:
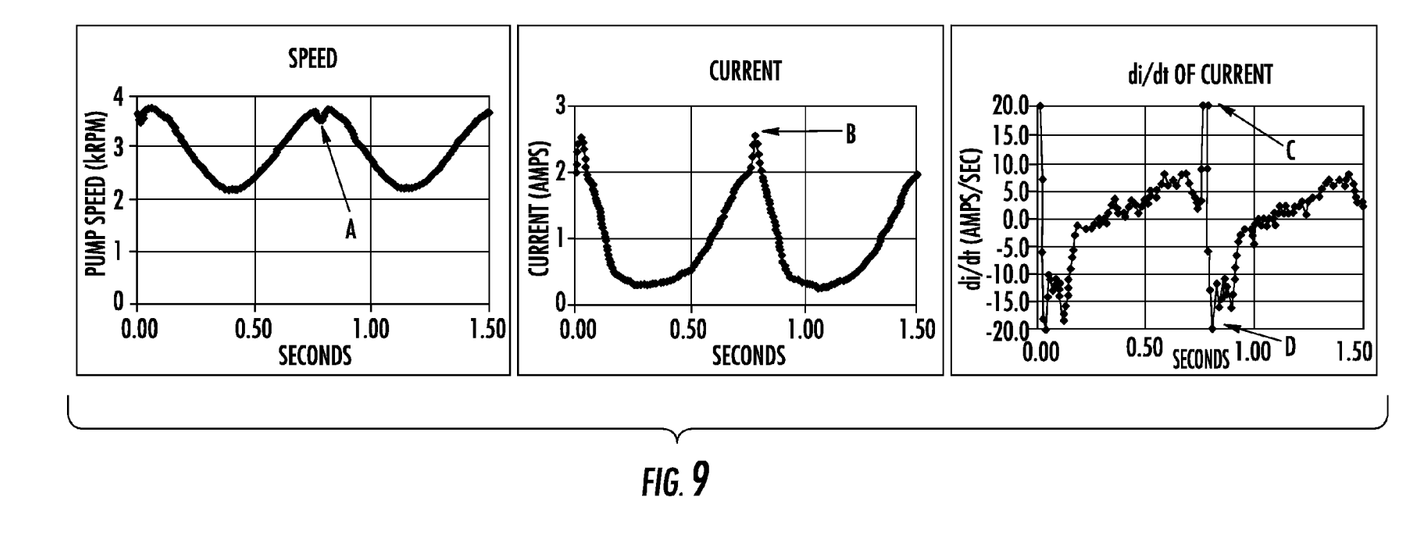
FIG. 9 is a set of graphs showing operation of an artificial heart with modulated speed which is experiencing intermittent suction.

Normally, when the speed is a sinusoidal speed wave form, this will yield a current of a similar wave form, and vice-versa. An example of normal system response is shown in FIG. 8, showing the sinusoidal speed and a near sinusoidal current. In this example, the pump speed was modulated at frequency of 1.33 Hz (i.e. 80 beats per minute), and an amplitude of +/−25% of the mean speed of 2800 RPM. In FIG. 9, the same modulation at a mean speed of 3000 RPM resulted in intermittent suction, with a non-sinusoidal speed/current relationship (indicated at "A" and "B"), and spikes in the rate of current change (di/dt), clearly indicating the point of rubbing (high positive di/dt) at "C" and period of suction (high negative di/dt) at "D". Based on these observations, a high absolute value of (di/dt) can serve as a predetermined limit or trigger for a response. The limit value for a particular application may be derived from empirical test data. Alternatively, the controller 32 may be programmed to evaluate the speed or current wave forms and trigger a response based on the existence of particular characteristics in the wave forms, such as the brief RPM drops indicated at A in FIG. 9, or the peak discontinuities shown at B in FIG. 9.

Figure 10:
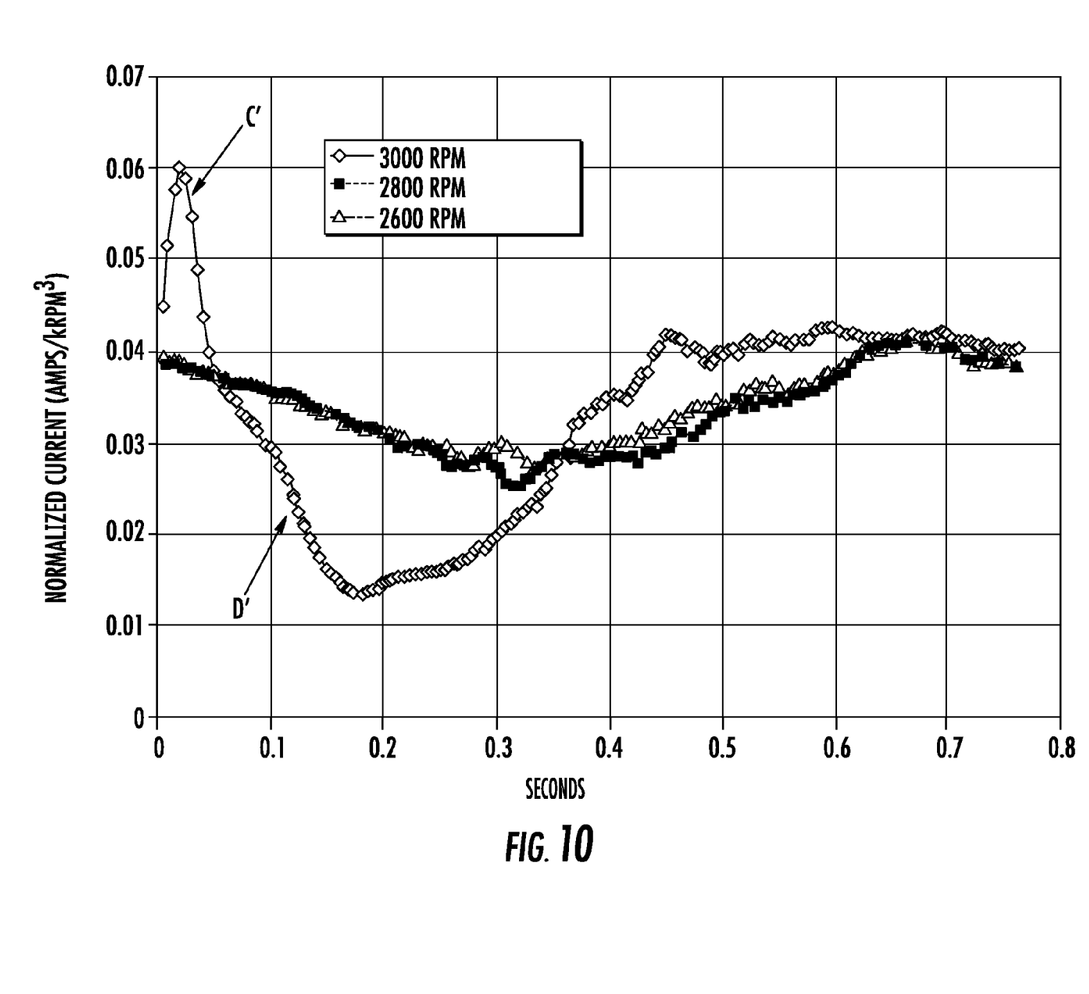
FIG. 10 is a graph showing normalized current flow versus time in an artificial heart operating at various speeds.
Figure 11:
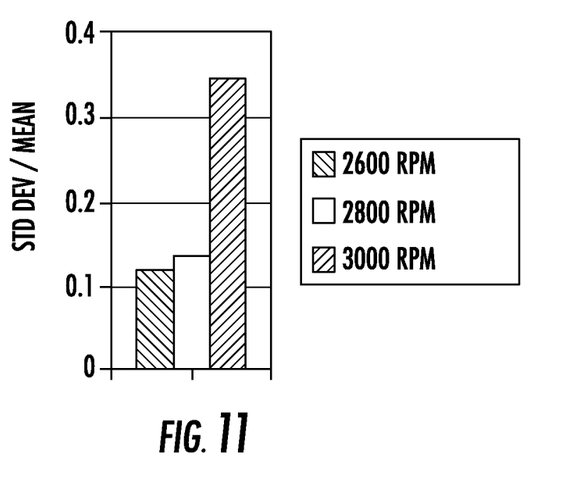
FIG. 11 is a graph of the statistical variation in the normalized current flow shown in FIG. 10.

Another suitable test for triggering peak speed reduction is analysis of normalized current. FIG. 9 shows normalized current (where the current signal is normalized by dividing by the cube of the speed signal) for an artificial heart 10 operating at 2600 RPM, 2800 RPM, and 3000 RPM. Normally, the resulting signal of current divided by speed cubed has small variation (see FIG. 11). However, when the speed is high enough to cause an abnormal suction condition, the variation in normalized current is dramatically higher. This is clearly seen in the example of operation at 3000 RPM. Rubbing is indicated at "C" and suction at "D" in FIG. 10, with a correspondingly high variation in normalized current in FIG. 11. Based on these observations, a high value of variation in normalized motor current can serve as a predetermined limit or trigger for a response. The limit value for a particular application may be derived from empirical test data.

Regardless of which specific trigger or limit value is used to determine the presence of suction and/or rubbing, the controller 32 may be programmed to evaluate the parameter and look for the specified trigger and/or compare the parameter to the predetermined limit. If suction or rubbing is indicated, the controller 32 responds by reducing the peak speed. This can be done by lowering the mean speed, reducing the speed modulation amplitude, changing the duty cycle (portion of time at high speed), or any combination thereof.

The foregoing has described a method of operating a total artificial heart. While specific embodiments of the present invention have been described, it will be apparent to those skilled in the art that various modifications thereto can be made without departing from the spirit and scope of the invention. Accordingly, the foregoing description of the preferred embodiment of the invention and the best mode for practicing the invention are provided for the purpose of illustration only and not for the purpose of limitation.

What is claimed is:

1. A method of controlling a pump including a electrical motor coupled to a rotor which carries first and second impellers at opposite ends thereof, the method comprising:
   (a) driving the rotor using the motor, so as to circulate fluid from the first impeller through a first fluid circuit, the second impeller, a second fluid circuit, and back to the first impeller;
   (b) sensing electrical power delivered to the motor and determining a resistance of the first fluid circuit, based on a first motor parameter of the motor which is proportional to the electrical power delivered to the motor;
   (c) determining a flow rate through the first fluid circuit based on a second motor parameter of the motor which is proportional to the electrical power delivered to the motor; and
   (d) varying at least one operational parameter of the pump so as to maintain a predetermined relationship between the flow rate and the resistance of the first fluid circuit.

2. The method of claim 1 wherein the at least one operational parameter is selected from the group consisting of: are mean pump speed, electrical pulse rate, speed pulsatility, and pump duty cycle, and combinations thereof.

3. The method of claim 1 further comprising modulating the speed of the rotor to generate a pulsatile flow.

4. The method of claim 3 further comprising varying the degree of speed change based on the resistance of the first fluid circuit.

5. The method of claim 1 further comprising allowing the rotor to move axially within a housing to vary the relative performance of the first and second impellers in response to changes in the flow rate in the first and second fluid circuits.

6. The method of claim 5 further comprising:
   (a) monitoring a third motor parameter of the motor indicative of suction or rubbing of the pump; and
   (b) in response to an indication of suction or rubbing, reducing a peak speed of the motor.

7. The method of claim 6 wherein the third motor parameter is the absolute value of the change in motor current.

8. The method of claim 6 wherein the third motor parameter is variation in normalized current input to the motor.

9. The method of claim 6 wherein the step of reducing the peak motor speed includes an action selected from the group consisting of: lowering a mean speed of the motor, reducing an amplitude of speed modulation, changing a duty cycle of the motor, and combinations thereof.

10. The method of claim 1 further comprising, prior to step (a):
   (a) coupling the first impeller with a patient's systemic vasculature; and
   (b) coupling the second impeller with a patient's pulmonary vasculature.

* * * * *